(12) United States Patent
Nakagawa et al.

(10) Patent No.: US 6,310,276 B1
(45) Date of Patent: Oct. 30, 2001

(54) PLANT WHICH BELONGS TO THE GENUS LIMONIUM AND A METHOD FOR CREATING THE SAME

(75) Inventors: Masahiro Nakagawa, Fukuroi; Takashi Hayama, deceased, late of Wada-machi, by Murako Hayama, Shizuo Hayama, heirs; by Michiko Kondo, heir, Muruyama-machi; by Chieko Matsuo, heir, Yotsukaido, all of (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/144,037

(22) Filed: Aug. 31, 1998

(30) Foreign Application Priority Data

Sep. 2, 1997 (JP) .................................... 9-237213
Jun. 25, 1998 (JP) .................................. 10-178417

(51) Int. Cl.[7] ............... A01H 5/00; A01H 5/10; A01H 1/04

(52) U.S. Cl. ............ 800/323; 800/298; 800/260; Plt./358

(58) Field of Search ............................. 800/298, 260, 800/269, 278, 289, 323; Plt./358

(56) References Cited

PUBLICATIONS

Azuma et al. Accleration of Flowering of Statice (*Limonium sinuatum* Mill.) by Seed Vernalization. Journal of Japanese Society of Horticultural Science. vol. 51, pp. 466–474, 1983.*

Burge et al. Generation of Novel Forms of Limonium. Acat. Horticulturae. vol. 420, pp. 78–80, 1995.*

Cohen et al. Selection for Early Flowering. Acta Horticulturae. vol. 420, pp. 118–124, 1995.*

Morgan et al. Interspecific hybridisation between *Limonium perigrinum* Bergius and *Limonium purpuratum* L. Euphytica. vol. 83, pp. 215–224, 1995.*

* cited by examiner

*Primary Examiner*—Paula Hutzell
*Assistant Examiner*—Melissa L. Kimball
(74) *Attorney, Agent, or Firm*—Oblon, Spivak, McClelland, Maier & Neustadt, P.C.

(57) ABSTRACT

A plant which belongs to the genus Limonium, having a characteristic of undergoing flower bud differentiation and flower stalk development within 50 days from seeding even without low temperatures of 25° C. or below; and a method for creating the plant are disclosed.

4 Claims, No Drawings

PLANT WHICH BELONGS TO THE GENUS LIMONIUM AND A METHOD FOR CREATING THE SAME

BACKGROUND OF THE INVENTION

1. Field of the Invention

The present invention relates to a novel plant which belongs to the genus Limonium and has a characteristic of undergoing flower bud differentiation without encountering low temperatures.

2. Description of the Background

Limonium plants, which are generally called statice, are ornamental plants used as cut flowers or the like. These plants have a characteristic that they do not form flower buds unless encountering low temperatures. Thus, generally, these plants are seeded in fall to meet with low temperatures in winter. Plants seeded in fall will flower around April to May in the next year.

In order to induce their flowering at an earlier stage (sometime from December to March), an artificial low temperature treatment must be given. At present, forcing culture of Limonium plants to achieve early flowering is carried out as described below.

In case of seedling propagation, seeds are sown in seeding boxes around August. One day after the seeding, when the seeds have absorbed moisture and become active, they are placed in a refrigerator at 2–4° C. for 30–40 days to induce flower bud differentiation with low temperature stimulation. Around September, the refrigerated seedlings are taken out of the refrigerator and raised in pots. Then, they are transplanted in a greenhouse in soil beds. When the temperature considerably drops around November, the inside of the greenhouse is heated to thereby promote flow stalk development and flowering.

In case of vegetative reproduction using herbaceous cuttings, mericlones or the like, axillary buds or apical meristems are collected from the plants with flower buds already differentiated. The seedlings resulting therefrom are grown under low temperature conditions. Then, they are planted in a greenhouse in fall. Thereafter, they are cultivated in the same manner as in seedling propagation.

Although the above-mentioned methods make it possible to induce the flowering of Limonium plants at an early stage, there have the following problems.

First, investment to facilities such as refrigerators to provide low temperatures is required.

Secondly, since seedlings are kept under darkness in a refrigerator (which is different from their natural growing conditions) for a long period, a large number of plant bodies are withered when they are taken out of the refrigerator.

Further, if the plants taken out of the refrigerator meet with high temperatures, flower stalk development will not occur due to devernalization. They will not flower unless they are vernalized again by low temperatures. In order to avoid devernalization, seeding time is chosen so as for the seedlings to be taken out of the refrigerator in the fall when the temperature is cool enough, or seedlings must be raised in the air-conditioned room until there is no danger of devernalization (i.e., the temperature is sufficiently low). In addition, when the seedlings raised in the air-conditioned room are planted in a greenhouse, the temperature of the greenhouse must be sufficiently low to prevent devernalization. Thus, flowering time can be advanced only to a certain extent, which is dependent on the temperature of the place of cultivation).

SUMMARY OF THE INVENTION

The problems described above are attributable to the property of Limonium plants that they will not flower unless they encounter low temperatures (i.e. low temperature requirement). Thus, these problems can be solved if a plant which can flower without low temperature requirement can be created.

It is an objective of the present to provide a plant which belongs to the genus Limonium without low temperature requirement for flowering from the above-mentioned viewpoint.

Toward the solution of the above problems, the present inventors have made intensive and extensive researches and, as a result, have found a Limonium line in the fields that flowers at an early stage. By repeating selection and mass-crossing using this line, the inventors have succeeded in fixing a line without low temperature requirement. The present invention has been achieved based on the thus fixed line.

The present invention relates to a plant which belongs to the genus Limonium, having a characteristic of undergoing flower bud differentiation and flower stalk development within 50 days from seeding even without exposure to low temperatures of 25° C. or below.

The present invention also relates to a method for creating the plant which belongs to the genus Limonium, which comprises the following steps: (i) crossing SG4-15 line or its progeny with another line which belongs to the genus Limonium; (ii) mass-crossing the resultant F1 hybrid; and (iii) selecting from the resultant F2 hybrid those individuals with a characteristic of undergoing flower bud differentiation and flower stalk development within 50 days from seeding even without exposure to low temperatures of 25° C. or below.

DETAILED DESCRIPTION OF THE PREFERRED EMBODIMENTS

Hereinbelow, the present invention is described in detail.

The term "a plant which belongs to the genus Limonium" used in the present invention primarily means a plant which belongs to *Limonium sinuatum*. However, "a plant which belongs to the genus Limonium" is not limited to this species.

The plant of the invention which belongs to the genus Limonium has a characteristic of undergoing flower bud differentiation and flower stalk development at an early stage even without exposure to low temperatures of 25° C. or below. The term "an early stage" used herein means within 50 days from seeding or a state of growth in which the number of leaves is 50 or less. Most of the conventional Limonium plants do not undergo flower stalk development and flower bud formation unless they encounter low temperatures of 25° C. or below. Although some varieties undergo flower stalk development under temperature conditions of 25° C. or above, the time of their flower stalk development is late; usually, it takes 100 days from seeding. No varieties are known that undergo flower stalk development within 50 days from seeding or in a state of growth in which the number of leaves is 50 or less.

The plant of the invention, belonging to the genus Limonium, can be created by (i) crossing a line which belongs to the genus Limonium which does not have low temperature requirement with another line which belongs to the genus Limonium; (ii) mass-crossing the resultant F1 hybrid; and (iii) selecting from the resultant F2 hybrid those individuals with a characteristic of undergoing flower bud differentiation and flower stalk development within 50 days from seeding without low temperatures of 25° C. or below; or those individuals with a characteristic of undergoing flower bud differentiation and flower stalk development in a state of growth in which the number of leaves is 50 or less even without low temperatures of 25° C. or below.

As the "line which belongs to the genus Limonium which does not have low temperature requirement" used in the invention, SG4-15 line or its progeny may be given, for example. Seeds of SG4-15 line are possessed by the applicant, who guarantees the release of these seeds stipulated in Article 27, Paragraph 3 of the Japanese Patent Law Enforcement Regulations. As the "another line which belongs to the genus Limonium", any of the existing Limonium varieties may be used. Specific examples include, but are not limited to, 'Early Blue', 'Gold Coast', 'American Beauty', 'Marine Blue' (from Dai-ichi Seed Co., Ltd.) and 'Sunday Pink' (from Miyoshi & Co., Ltd.). The characteristic of non-low-temperature requirement which SG4-15 line has is inherited recessively. Thus, this characteristic is not expressed in F1 generation, but one fourth of the F2 population is expected theoretically to have this characteristic.

Seeds of SG4-15 line have been deposited with the National Institute of Bioscience and Human Technology Agency of Industrial Science and Technology (1-3, Higashi 1-chome, Tsukuba-shi, Ibaraki-ken 305, Japan, on Jun. 16, 2000) under the terms of the Budapest Treaty, and received an accession number FERM BP-7189.

PREFERRED EMBODIMENTS OF THE INVENTION

EXAMPLE 1

In a field where a cultivar called 'Early Blue' was cultivated, the present inventors found an individual which undergoes flower stalk development and flowering at an especially early stage. It was presumed that this individual has the characteristic of undergoing flower bud differentiation even under high temperatures.

Then, seeds were collected from the individual and cultivated under high temperature conditions under which flower bud differentiation would not occur in conventional Limonium varieties. From the resultant plants, a line which forms flower buds early was selected repeatedly. As a result of mass-crossing and selection of more than 10 times, a line without low temperature requirement, which forms flower buds without low temperatures, has been fixed. This line was designated "SG4-15 line".

EXAMPLE 2

A cultivation trial on the three varieties of SG4-15 line, 'Early Blue' and 'Gold Coast' was conducted at the Kimitsu Breeding Station of Sakata Seed Corporation during March 1996 to examine the time of flower stalk development. Among the existing varieties, 'Gold Coast' is the variety which requires low temperature least (Semeniuk, P. and Krizek, D. T., Journal of the American Society for Horticultural Science, Vol. 98, No. 2, pp. 140–142 (1973)). This cultivation trial was conducted at 28° C. under constant temperature conditions and under natural light. For each variety, 30 individuals were tested. The results are shown in Table 1.

TABLE 1

Relation between Days after Seeding and Flower Stalk Development

| Line | Percentage of plants with flower Stalk development | | | | Average No. of leaves at the time of flower stalk development |
|---|---|---|---|---|---|
| | 50 days after seeding | 60 days after seeding | 70 days after seeding | 90 days after seeding | |
| SG4-15 line | 53.6 | 92.9 | 96.4 | 100.0 | 24.1 |
| 'Gold Coast' | 0 | 3.3 | 13.3 | 23.3 | 81.2 |
| 'Early Blue' | 0 | 0 | 0 | 0 | — |

SG4-15 line: Although the time of flower stalk development varied among individuals, flower stalk development was confirmed in half of the individuals 50 days after seeding and in most of them 60 days after seeding. All of the individuals underwent flower stalk development and flowered within about 90 days from seeding.

'Early Blue': Flower stalk development was not confirmed in any individual 90 days after seeding.

'Gold Coast': Flower stalk development was confirmed in only one individual out of thirty plants 60 days after seeding (flower stalk development ratio: 3.3%). Flower stalk development was confirmed in seven individuals out of thirty plants 90 days after seeding. However, any of these individuals has not reached flowering 90 days after seeding.

EXAMPLE 3

A cultivation trial on the three varieties of SG4-15 line, 'Early Blue' and 'Gold Coast' was conducted at the Kimitsu Breeding Station of Sakata Seed Corporation to examine the time of flower stalk development. This cultivation trial was conducted under three different temperature conditions of at 28° C., 31° C. or 34° C. and under natural light. For each variety, 20 individuals were tested.

When the temperature was set at 31° C. or 34° C., flower stalk development was not observed in any of the tested varieties because of their poor growth due to high temperatures. When the temperature was set at 28° C., flower stalk development was observed in SG4-15 line alone 60 days after seeding. It was presumed that the delay in the time of flower stalk development compared to the results in Example 2 is attributable to the low quantity of light during this trial.

EXAMPLE 4

A cultivation trial on the four varieties of SG4-15 line, 'Early Blue', 'Gold Coast' and 'American Beauty' was conducted at the Kakegawa Breeding Station of Sakata Seed Corporation in January 1997 to examine the time of flower stalk development. This cultivation trial was conducted keeping the temperature at 25–28° C. under natural light. The quantity of light for this experiment was low as a result of vinyl film coating on green house for thermal insulation. The results are described below.

SG4-15: Flower stalk development was confirmed in 18 individuals out of 25 (flower stalk development ratio: 72%) 90 days after seeding (number of leaves: about 24).

'Early Blue': Flower stalk development was not confirmed in any of the 19 individuals tested 90 days after seeding.

'Gold Coast': Flower stalk development was confirmed in 5 individuals out of 22 (flower stalk development ratio: 22%) 90 days after seeding.

'American Beauty': Flower stalk development was not confirmed in any of the 22 individuals tested 90 days after seeding.

possible flower stalk development was completed. The results are shown in Table 2.

TABLE 2

|  |  | 80 Days after Seeding | | | | | |
|---|---|---|---|---|---|---|---|
|  | No. of Individuals Tested | No. of individuals which have not undergone flower stalk development | No. of individuals which have undergone flower stalk development | Flower Stalk Development Ratio | Expected Segregation Ratio in F2 Population |  | $\chi^2$ |
| SG4-15 |  | 30 | 0 | 30 | 100 |  |  |
| 'Gold Coast' |  | 20 | 17 | 3 | 15 |  |  |
| 'American Beauty' |  | 30 | 30 | 0 | 0 |  |  |
| 'Forever Silver' |  | 30 | 30 | 0 | 0 |  |  |
| SG4-15 x 'American Beauty' | F1 | 40 | 40 | 0 | 0 |  |  |
| 'American Beauty' x SG4-15 | F1 | 40 | 40 | 0 | 0 |  |  |
| SG4-15 x 'Forever Silver' | F1 | 40 | 40 | 0 | 0 |  |  |
| 'Forever Silver' x SG4-15 | F1 | 40 | 40 | 0 | 0 |  |  |
| 5G4-15 x 'Marine Blue' | F2 | 516 | 388 | 128 | 24.81 | 3:1 | 0.010 | P > 0.9 |
| 5G4-15 x 'Flush Lavender' | F2 | 1040 | 780 | 260 | 25 | 3:1 | 0.000 | P > 0.9 |
| 'American Beauty' x SG4-15 | F2 | 906 | 693 | 213 | 23.51 | 3:1 | 1.073 | 0.3 > P > 0.2 |
| 5G4-15 x 'Forever Silver' | F2 | 831 | 608 | 223 | 26.84 | 3:1 | 1.493 | 0.3 > P > 0.2 |
| 'Forever Silver' x SG4-15 | F2 | 601 | 451 | 150 | 24.96 | 3:1 | 0.001 | P > 0.9 |

EXAMPLE 5

A cultivation trial on F1 hybrid between SG4-15 and 'American beauty', F2 hybrid between SG4-15 and 'Marine Blue ' and F2 hybrid between SG4-15 and 'Sunday Pink' was conducted at the Kakegawa Breeding Station of Sakata Seed Corporation to examine whether they have undergone flower stalk development 90 days after seeding. The temperature and light conditions were the same as in Example 4.

F1 (SG4-15x'American Beauty'): Flower stalk development was not confirmed in any of the 20 individuals tested.

F2 (SG4-15x'Marine Blue'): Flower stalk development was confirmed in 41 individuals out of the 74 tested (flower stalk developed: flower stalk undeveloped=1:2).

F2 (SG4-15x'Sunday Pink'): Flower stalk development was confirmed in 27 individuals out of the 93 tested (flower stalk developed: flower stalk undeveloped=1:3).

The property of non-low-temperature requirement which SG4-15 line has is not expressed in F1 generation at all. In F2 generation, the segregation ratio of individuals expressing this property against individuals not expressing this property is approximately 1:3. From these findings, it was presumed that the property of non-low-temperature requirement of SG4-15 is inherited in the mode of single factor recessive inheritance.

EXAMPLE 6

Seeds of SG4-15, seeds of existing varieties, and F1 and F2 seeds obtained by crossing SG4-15 with existing varieties were seeded in 128-holed plug trays on Jul. 31, 1997. Two weeks after the seeding, the resultant seedlings were potted in pots 9 cm diameter. They were cultivated under control in such a manner that they do not encounter with low temperatures 25° C. or below. Flower stalk development was examined 80 days after seeding. In F2 generation, many individuals underwent flower stalk development more than 60 days after seeding; and it was judged that flower buds had already been formed in some stocks in which flower stalk development was not confirmed 60 days after seeding. Thus, final examination was performed 80 days after seeding when Flower stalk development was observed in all of the individuals of SG4-15, whereas it was hardly observed in existing varieties. Particularly, no individuals underwent flower stalk development in 'American Beauty' and Forever Silver. Also, no flower stalk development was observed in F1 hybrids between SG4-15 and existing varieties. In contrast, flower stalk development was observed in a large number of individuals in F2 hybrids between SG4-15 and existing varieties.

Building up a hypothesis that the segregation ratio of flower stalk-undeveloped individuals against flower stalk-developed individuals in F2 hybrids will be 3:1, the inventors examined it with $\chi^2$ test (Susumu Ishii, "Introduction to Statistics in Biology", Baifukan Co.). As a result, it was concluded that this hypothesis fits.

EXAMPLE 7

The statice stocks which had been grown from the previous year as trial products were cut in June, 1997 to collect herbaceous cuttings. Although it was impossible to make the size of the cuttings uniform, cuttings with about 4 foliage leaves were prepared and planted in a cutting bed. After confirmation of their rooting, they were potted in 9 cm pots. Thereafter, they were grown according to the conventional methods. The temperature environment was not particularly controlled, but about 40% shading was carried out in August. The number of individuals which had undergone flower stalk development was counted on September 25. The results are shown in Table 3.

TABLE 3

| Line | No. of Stocks Tested | No. of stocks which underwent flower stalk development | Flower stalk development ratio |
|---|---|---|---|
| SG4-15 | 40 | 40 | 100 |
| 'Early Blue' | 20 | 0 | 0.0 |
| 'Marine Blue' | 32 | 6 | 18.8 |
| 'Flush Pink' | 26 | 0 | 0.0 |

TABLE 3-continued

| Line | No. of Stocks Tested | No. of stocks which underwent flower stalk development | Flower stalk development ratio |
|---|---|---|---|
| 'American Beauty' | 18 | 0 | 0.0 |
| 'Forever Silver' | 15 | 0 | 0.0 |

Flower stalk development was hardly observed in the existing varieties of 'Early Blue', 'Marine Blue', 'Flush Pink', 'American Beauty' and 'Forever Silver'. In one variety, those which undergo flower stalk development and those which do not segregated. However, since all of the individuals which belongs to one variety were obtained from one same individual by vegetative reproduction, it is considered that the above segregation was brought about not by hereditary factors but by environmental factors such as the state of the cuttings used.

In contrast, all of the individuals which belongs to SG4-15 line underwent flower stalk development. From this, it is considered that SG4-15 line does not need low temperatures for flower bud differentiation and that this line is hard to get devernalized even encountering with high temperatures.

The present invention provides a novel plant which belongs to the genus Limonium. Since this plant undergoes flower stalk development and flowering without low temperatures, complicated operations and high cost facilities to provide low temperatures are not necessary. Furthermore, seeding, planting and flower harvesting of this plant can be possible out anytime throughout a year, without worrying about outer temperature at the time of taking out seedlings from a refrigerator or transplanting, or the temperature of the inside of a greenhouse. In addition, the period from seeding to harvesting of this plant is short and, thus, the cultivation period can be minimized to thereby save the cultivation cost.

What is claimed is:

1. A plant belonging to *Limonium sinuatum*, which undergoes flower bud differentiation and flower stalk development within 50 days from seeding without exposure to low temperatures of 25° C. or below, which plant is obtained from SG4-15 line (accession number FERM BP-7189) or a progeny thereof.

2. A method for producing a plant belonging to *Limonium sinuatum*, which undergoes flower bud differentiation and flower stalk development within 50 days from seeding without exposure to low temperatures of 25° C. or below, which comprises:

a) crossing SG 4-15 line (accession number FERM BP-7189) with another line which belongs to *Limonium sinuatum;* b) mass crossing the resultant F1 hybrid; and c) selecting from the resultant F2 hybrid those individuals which undergo flower bud differentiation and flower stalk development within 50 days from seeding without exposure to low temperatures of 25° C. or below.

3. Seeds of a plant belonging to *Limonium siniatum*, which under goes flower bud differentiation and flower stalk development within 50 days from seeding without exposure to low temperatures of 25° C. or below, which seeds are obtained from SG4-15 line (accession number FERM BP-7189) or a progeny thereof.

4. Cuttings of a plant belonging to *Limonium siniatum*, which undergoes flower bud differentiation and flower stalk development within 50 days from seeding without exposure to low temperatures of 25° C. or below, which plant is obtained from SG4-15 line (accession number FERM BP-7189) or a progeny thereof.

\* \* \* \* \*

UNITED STATES PATENT AND TRADEMARK OFFICE
CERTIFICATE OF CORRECTION

PATENT NO.     : 6,310,276 B1                                                   Page 1 of 1
DATED          : October 30, 2001
INVENTOR(S)    : Nakagawa et al.

It is certified that error appears in the above-identified patent and that said Letters Patent is hereby corrected as shown below:

<u>Title page, Item [54], and Column 1, line 4,</u>
The title should read:
-- [54] PLANT BELONGING TO LIMONIUM SINIATUM AND A METHOD OF PRODUCING THE SAME --
Item [75], the Inventors should read:
-- [75] Inventors: Masahiro Nakagawa, Fukuroi; Takashi Hayama, deceased, late of Awa-gun, by Murako Hayama, Shizuo Hayama, Michiko Kondo, heirs, all of Awa-gun; by Chieko Matsuo, heir, Yotsukaido-shi, all of (JP) --

Signed and Sealed this

Ninth Day of July, 2002

*Attest:*

JAMES E. ROGAN
*Attesting Officer*  *Director of the United States Patent and Trademark Office*